(12) United States Patent
Hu (10) Patent No.: US 7,106,075 B2
(45) Date of Patent: Sep. 12, 2006

(54) ONLINE FLUID CONTAMINANT DETECTOR

(76) Inventor: Shenggen Hu, 22 Barcoorah Street, Westlake QLD 4074 (AU)

( * ) Notice: Subject to any disclaimer, the term of this patent is extended or adjusted under 35 U.S.C. 154(b) by 0 days.

(21) Appl. No.: 10/486,760

(22) PCT Filed: Aug. 9, 2002

(86) PCT No.: PCT/AU02/01070

§ 371 (c)(1),
(2), (4) Date: Jul. 7, 2004

(87) PCT Pub. No.: WO03/014729

PCT Pub. Date: Feb. 20, 2003

(65) Prior Publication Data

US 2004/0239344 A1 Dec. 2, 2004

(30) Foreign Application Priority Data

Aug. 9, 2001 (AU) .................................. PR6922

(51) Int. Cl.
*G01R 27/26* (2006.01)
(52) U.S. Cl. ...................................... 324/698; 324/663
(58) Field of Classification Search .............. 73/53.05; 324/204, 439, 691, 698, 663
See application file for complete search history.

(56) References Cited

U.S. PATENT DOCUMENTS

| | | | |
|---|---|---|---|
| 4,701,713 A | 10/1987 | Eaton et al. | |
| 5,179,346 A * | 1/1993 | McGee et al. | 324/693 |
| 5,370,776 A | 12/1994 | Chen | |
| 5,852,404 A | 12/1998 | Amini | |
| 6,577,112 B1 * | 6/2003 | Lvovich et al. | 324/71.1 |
| 6,844,745 B1 * | 1/2005 | Schachameyer et al. | 324/698 |

FOREIGN PATENT DOCUMENTS

| | | |
|---|---|---|
| DE | 197 06 486 | 8/1998 |
| DE | 197 08 067 | 9/1998 |
| EP | 0 922 963 | 6/1999 |
| EP | 1 014 082 | 6/2000 |
| EP | 1 098 196 | 5/2001 |
| EP | 1 098 197 | 5/2001 |
| EP | 1 111 383 | 6/2001 |
| GB | 2 306 660 | 5/1997 |
| WO | WO 98/52073 | 5/1998 |
| WO | WO 99/58965 | 11/1999 |

OTHER PUBLICATIONS

Search Report in PCT/AU02/01070, Sep. 27, 2002, Australia.

* cited by examiner

*Primary Examiner*—Walter Benson
(74) *Attorney, Agent, or Firm*—Kenyon & Kenyon LLP (57) ABSTRACT

A method for detecting extraneous matter in a fluid including the steps of applying an energy source to electrodes located in a fluid, measuring real and imaginary electrical impedance values across the electrodes for a plurality of different frequencies of alternating energy and identifying at least one characteristic of an extraneous matter in the fluid.

36 Claims, 12 Drawing Sheets

ONLINE FLUID CONTAMINANT DETECTOR

FIELD OF THE INVENTION

The present invention relates to analysis of fluids such as oil. The invention is particularly concerned with monitoring fluid quality for extraneous matter such as contaminants.

BACKGROUND TO THE INVENTION

It has been estimated that the repairs and down time caused by oil-related engine or other machine failures represent about 30–50% of the operation cost in Australian mining industry. In the economies of developed countries the damage from machine and engine wear represents about 6% of the gross national product. Thus, the development of effective techniques for the reliable prognosis of wear and maintaining the effectiveness of working lubrication oils is of substantial interest. Current diagnostic tests based on Scheduled Oil Sampling can not promptly detect a rapidly progressing component failure or a sudden ingestion of oil contaminants.

Furthermore, in many situations the timing of any oil change is associated with the measured use of the vehicle or machine using the oil rather than the actual condition of the oil. Ideally it would be desirable to monitor the condition of the oil so that information can be obtained about deterioration or contamination in the oil before any catastrophic failure of the machine or machine components can take place.

Different methods have been adopted for monitoring the condition of oil. For example, the specification of U.S. Pat. No. 4,831,362 discloses an apparatus for detecting ferromagnetic particles in lubricating oil. The apparatus consists of two windings inductively coupled via the lubricating oil. A permanent magnet located behind a sensor winding generates a magnetic flux which attracts ferromagnetic particles giving rise to pulses in the sensor winding.

U.S. Pat. No. 5,262,732 describes a system which utilises both a permanent magnet and electro magnet to simultaneously impose their magnetic fields upon the lubricating oil so as to attract ferromagnetic particles in the oil.

U.S. Pat. No. 6,204,656 discloses an array of sensors in conjunction with a magnetic field intensity gradient to obtain a particulate distribution of ferrous particles across the array. Unfortunately, the systems of both of these patents are sensitive to mechanical vibration commonly encountered in moving machines. Furthermore, only limited information can be obtained about degradation of the oil which is being monitored.

Other systems have also been devised for monitoring oil contamination, such as those that measure dielectric constant. However, there is no system which is currently able to monitor a range of oil contaminants and which may be applicable to analysis and monitoring of other fluids.

SUMMARY OF THE INVENTION

The present invention relates to a method and assembly for detecting extraneous matter in a fluid. According to one embodiment of the invention an on-line detection system for lubrication oils is provided based on an Electrical Impedance Spectroscopy technique. This detector system is capable of providing on-line information on the type and extent of contaminants and oil degradation, particularly the concentration and average size of ferrous wear particles. The information may enable an early detection of problems before they lead to costly repairs and down time.

According to one aspect of the present invention there is provided a method for detecting extraneous matter in a fluid including the steps of applying an energy source to electrodes located in a fluid, measuring real and imaginary electrical impedance values across the electrodes for a plurality of different frequencies of energy and identifying at least one characteristic of at least one type of extraneous matter in the fluid based on changes in the real and imaginary electrical impedance measured for the plurality of different frequencies.

It is preferred that the method is able to detect the type and level of extraneous matter in a fluid and to identify the type and/or level of extraneous matter in the fluid.

It is preferred that the energy source provides an alternating current or voltage to the electrodes.

The electrodes may be configured in one or more pairs so as to provide a voltage drop across the pairs of electrodes.

It is preferred that the electrodes are configured with a plurality of first electrodes connected together and a plurality of second electrodes connected together.

Real and imaginary impedance values preferably include real and imaginary components of mathematically related parameters such as impedance, admittance, modulus and dielectric permittivity, etc.

Preferably the method includes identifying one or more features of extraneous matter present in the fluid.

The extraneous matter preferably includes matter such as gas, solid, liquid or energy such as heat, electric charge, etc or different combinations of the above.

According to one embodiment, the invention involves measuring the real and imaginary parts of the impedance at a selected frequency or over a frequency range of 0.1 Hz to 1 MHz.

The measuring step may include displaying a frequency spectrum for the real and imaginary parts of the impedance.

It is preferred that the method includes the step of measuring temperature of the fluid at each measurement frequency or measured impedance spectrum.

The method may include the step of displaying and/or producing a frequency spectrum for the real and imaginary impedance values.

The method may include the step of displaying an impedance spectrum in the form of a complex plane plot of imaginary vs. real impedance values or in the plotting of quantities derived from the real and imaginary impedance values.

Preferably the method includes the step of determining concentration and/or average particle size of ferrous wear particles.

It is preferred that concentration and/or size of ferrous wear particles is determined from the impedance spectrum.

The frequency range is preferably between 0.1 Hz and 1 MHz.

The method may include the step of determining the extraneous matter from the impedance spectrum measured.

Preferably the method includes the step of determining the number of peaks and/or position of peaks in the measured impedance spectrum.

It is also preferred that the method includes the step of determining the height of peaks and/or the relative height of peaks in the measured impedance spectrum.

The method may include the step of measuring the impedance spectrum over a predetermined period of time.

According to one embodiment, the method includes the step of measuring the impedance at a selected frequency over a period of time.

The method preferably includes the step of analysing the impedance spectrum and producing a graph of impedance spectrum peak height versus degree of extraneous matter such as oxidation degree.

It should be noted that reference to impedance spectrum refers to EIS (Electrical Impedance Spectrum).

The extraneous matter preferably includes soot, water, coolant, diesel, ferrous particles, oxidation products.

It is preferred that the method includes measurement from the EIS of matter concentration and size, type of fluid etc.

It is preferred that the method includes the step of applying a magnetic field to attract ferrous particles between the electrodes, whereby the gap between the electrodes is able to be filled by a packed bed of the ferrous particles.

Preferably the magnetic field is generated using a DC electromagnet.

The method may include measuring electrical impedance at a selected frequency across the packed bed of ferrous particles in the gap between the electrodes for a period of time.

The method may include providing a graphical display of one or more characteristics of extraneous matter measured in the fluid.

Preferably the particle concentration is determined from the rate of change of impedance in the gap between the electrodes.

The method may include providing a first and second set of electrodes, the first set for detecting ferrous particles and the second set for detecting other extraneous matter.

The method preferably includes providing a magnetic field generation means for generating a magnetic field through a region in which the first set of electrodes is located.

The magnetic field is preferably applied by a DC electromagnet.

The first set of electrodes may be mounted to a non-conductive substrate which is perpendicular to the axis of the magnet.

The size of the first set of electrodes is preferably much smaller than the second set of electrodes.

A first set of electrodes is preferably aligned axially to the flow of fluid down stream of the second set of electrodes.

Preferably the method includes the step of analysing the impedance spectrum using pattern recognition algorithms to identify the type and/or level of extraneous matter in the fluid.

Preferably the method includes the step of determining whether a particular matter is present in the fluid by determining the change of characterization parameters of the impedance spectrum.

According to another aspect of the present invention there is provided an assembly for detecting extraneous matter in a fluid comprising a first set of electrodes located in a fluid chamber, the electrodes being aligned axially with the flow of fluid through the fluid chamber, a measuring device connected to the electrodes for measuring real and imaginary impedance values across the electrodes for a plurality of frequencies, whereby a data processor is able to display changes in the real and imaginary impedance values for the plurality of different frequencies.

It is preferred that the measuring device is adapted to measure the electrical impedance spectrum across the electrodes.

It is preferred that the apparatus includes a second set of electrodes located in the fluid chamber and connected to the measuring device for detecting a different extraneous matter to that detected by the first set of electrodes.

The first set of electrodes is preferably located downstream of the second set of electrodes.

The assembly may include a magnetic field generator such as an electromagnet.

The assembly preferably includes an adaptor housing with a fluid chamber in which the electrodes are located.

It is preferred that the method includes the step of determining whether a particular matter is present in the fluid by determining the change of characterisation parameters, such as first and second auto derivatives, average values of imaginary impedance component over a selective range of real impedance, and etc. extracted from the measured impedance spectrum.

Preferably the step of calculating the rate of impedance decrease from the average slope of the curve of relative impedance vs. time in the initial 50 seconds starting from when the magnetic field is applied to the first set of electrodes.

It is preferred that the method includes recording a curve of impedance magnitude versus time and converting the curve into a curve of relative impedance, which is defined as the ratio of impedance magnitude to the impedance magnitude without any ferrous particles in the gap, versus time.

According to a further aspect of the present invention there is provided a method of analysing extraneous matter in a fluid including the steps of receiving impedance data, being data including real and imaginary impedance values measured across electrodes located in a fluid, recording the impedance spectrum at a plurality of time intervals, calculating the peak height of the impedance spectrum for the received impedance data, comparing the peak height of the impedance spectrum with a reference impedance spectrum peak height and determining a feature of the extraneous matter from the comparing steps.

The method preferably includes determining how many peaks are present in the impedance spectrum of the received data.

The method may include the step of determining whether a particular matter is present by the number of peaks in the impedance spectrum and the height of the or each peak.

Preferably the method includes the step of determining whether a particular matter is present by determining the height of a single peak or the impedance spectrum and determining whether this is within a predetermined range such as 30 to 50 K$\Omega$.

The range of 30 to 50 K$\Omega$ may change as the configuration of the electrodes changes.

It is preferred that the data processor is programmed to display the change of impedance magnitude over a period of time.

The method may include the step of determining whether a particular matter is present by determining if the or each peak of the impedance spectrum is deformed and has a significant tail.

The method may include the step of determining whether a particular matter is present by determining if the or each peak of the impedance spectrum is deformed and has a significant tail in a range of low frequency.

Accordingly, the present invention provides a method of detecting contamination in a fluid, the method including:

applying an electric field to an electrode pair supported within a fluid and measuring changes in field characteristics between the fluid and an uncontaminated sample of the same fluid.

The method may also include applying a magnetic field to the fluid in the vicinity of the electrode pair in order to attract ferrous particles to the electrode pair.

The present invention also provides apparatus for detecting contaminants in a fluid, the apparatus including an electrode pair supported on a non-conductive base for emersion in a fluid, means for applying an electric field to the electrodes, and measuring means for measuring changes in field characteristics.

The apparatus may also include means for applying a magnetic field in the vicinity of the electrode pair.

BRIEF DESCRIPTION OF THE DRAWINGS

Preferred embodiments of the present invention will now be described by way of example only with reference to the accompanying drawings in which.

DETAILED DESCRIPTION OF THE INVENTION

It should be noted that values of impedance shown in the Figures are given in ohms.

Figure 1:
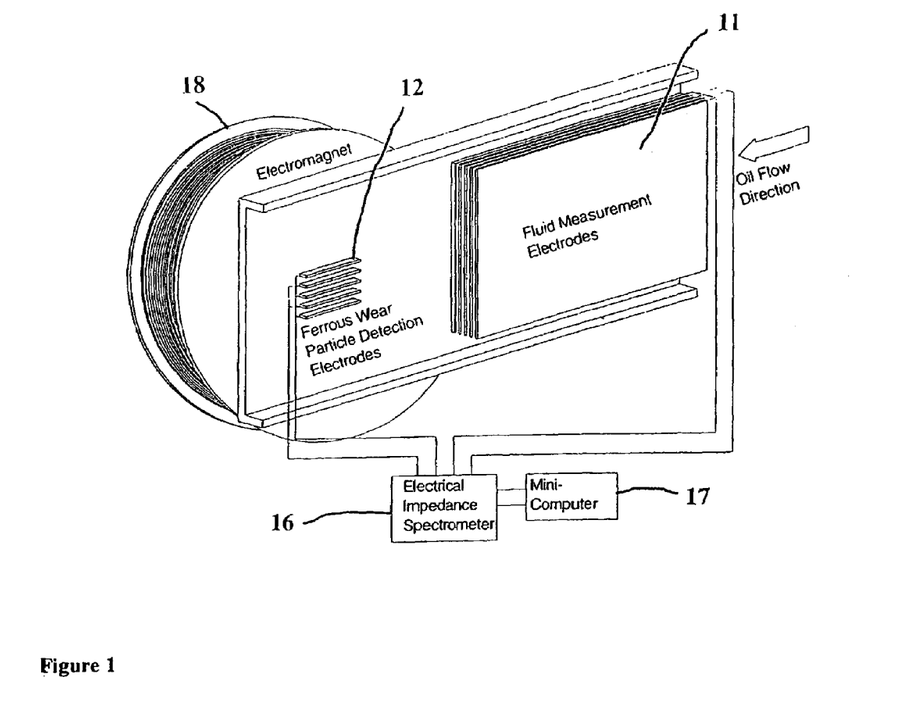
FIG. 1 shows a schematic diagram of an assembly for detecting extraneous matter in a fluid according to a first embodiment of the present invention.
Figure 13:
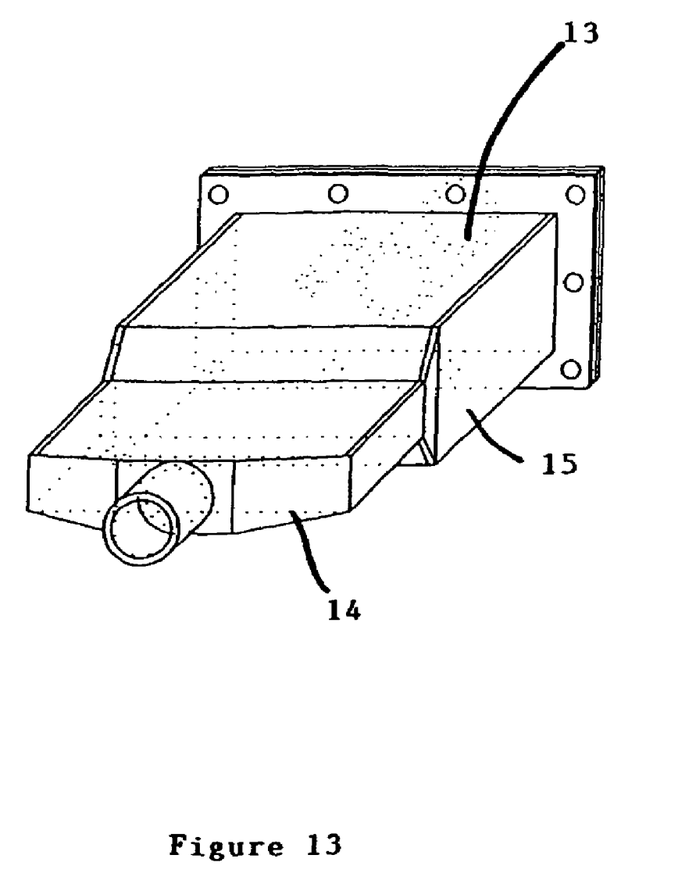
FIG. 13 shows an adaptor for housing the assembly shown in FIG. 1.

As shown in FIG. 1 an assembly for detecting extraneous matter in a fluid consists of a set of fluid measurement electrodes 11 typically spaced 1.6 mm apart and a set of ferrous wear particle detection electrodes 12 typically 0.6 mm apart. These electrodes are located in a fluid stream in an adaptor housing 13 as shown in FIG. 13.

The fluid measurement electrodes 11 are much larger than the ferrous particle detection electrodes 12 and are located upstream of the ferrous particle detection electrodes 12.

The ferrous particle detection electrodes 12 are also aligned in parallel at right angles together to the axis of alignment of the fluid measurement electrodes 11.

The ferrous particle detection electrodes being much smaller than the fluid measurement electrodes 11 are located in a smaller fluid chamber 14 of the adaptor 13.

A DC electromagnet 18 is located in close proximity to the fluid chamber 14 so as to provide a magnetic field through this chamber.

The other chamber 15 in which the fluid measurement electrodes are provided is preferably isolated from the chamber 14.

Each set of electrodes consists of successive pairs of electrodes with alternate electrodes of each pair electrically connected together.

An electrical impedance spectrometer 16 is connected to each of the sets of electrodes as well as to a data processor such as a mini computer 17.

In operation oil flows through the adaptor 13 and passes between the plates of the fluid measurement electrodes 11 and the ferrous wear particle detection electrodes 12.

By energising the electromagnet or solenoid 18 a magnetic field is established through chamber 14.

The electrical impedance spectrometer 16 is then operated to record the electrical impedance across the electrodes 12 at a selected frequency typically 10 kHz.

Figure 10A:
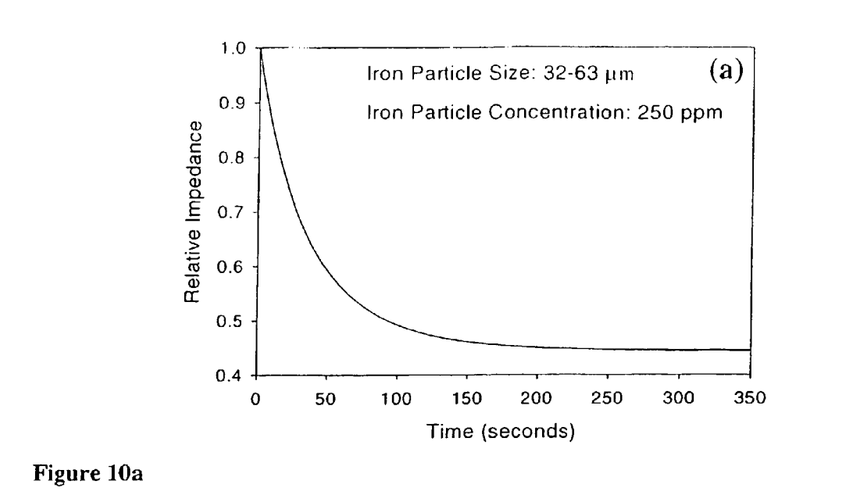
FIG. 10a shows a graphical representation of impedance vs. time between particle detecting electrodes reaching a limiting value when the gap is fully filled with ferrous particles, in accordance with one embodiment of the invention.

Under the effects of the magnetic field ferrous wear particles in the oil such as lubrication oil will be moved into the gap between the electrodes. Over a period of time ferrous particles will gradually fill the gap between each pair of electrodes and finally the electrodes 12 will be completely buried in a pile of ferrous particles. Therefore, over a period of time the impedance across each pair of electrodes will gradually decrease until the impedance is approaching a limiting value as shown in FIG. 10a.

The higher the concentration of ferrous particles the shorter the time interval between a limiting value of the impedance across the electrodes 12 is approached.

Due to the enrichment effect of the magnetic field and the use of a narrow gap between each pair of electrodes the assembly is able to detect iron particles with a concentration as low as a few parts per million.

By using a number of pairs of electrodes as in FIG. 1 the sensitivity of the assembly is increased further.

The use of a strong magnetic field allows most of the ferrous particles, including the size range of 5 to 20 micrometers, to travel from the bulk oil phase into the gap between the electrodes.

Figure 10B:
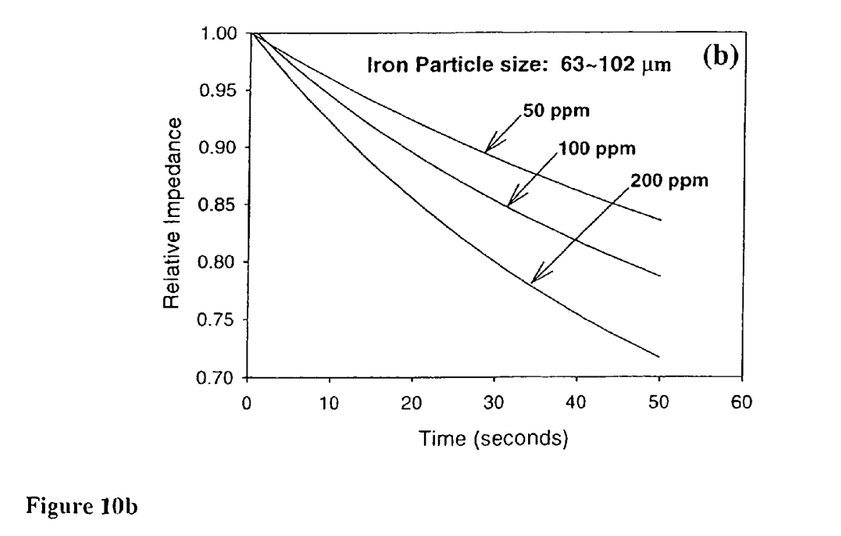
FIG. 10b shows a graphical representation of impedance versus time across electrodes in a fluid according to one embodiment of the present invention.

As shown in FIG. 10b the effect of concentration of iron (ferrous) particle on the measured relative impedance decreases with time during the time of ferrous particles having the size range 63 to 102 micrometers accumulate in the gap between the electrodes. The relative impedance is defined as the ratio of the impedance in the gap having the action of magnetic field to that without any ferrous particles in the gap. Thus FIG. 10b shows how the impedance in the gap between electrodes 12 for the case with the higher ferrous particle concentration, for example 200 parts per million (PPM) decreases faster than those for lower ferrous particle concentration.

Figure 11:
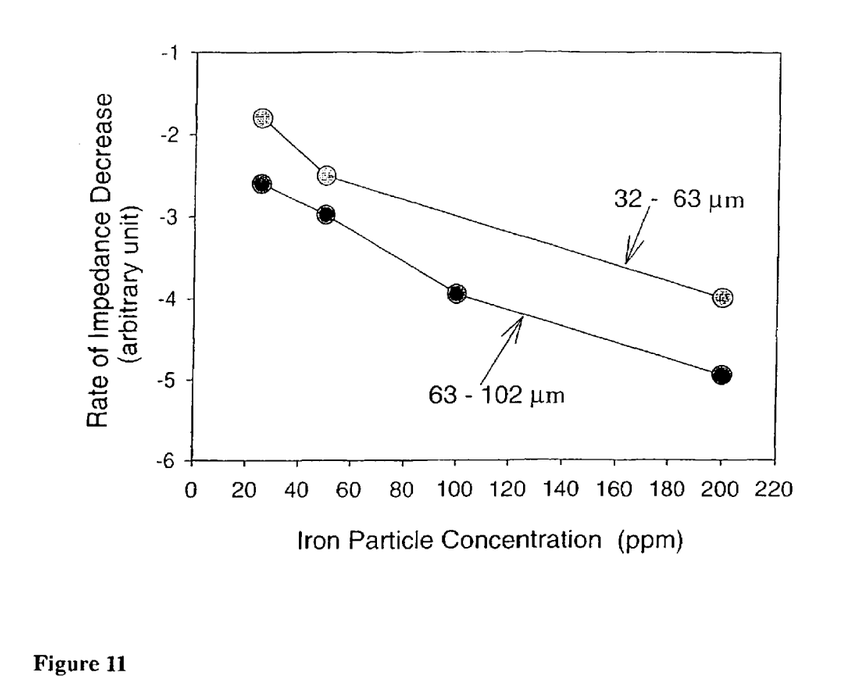
FIG. 11 shows a graphical representation of rate of impedance decrease versus iron particle concentration in accordance with one embodiment of the present invention.

The effect of iron particle concentration and size on the rate of impedance decrease is shown in FIG. 11. The rate of impedance decrease is defined as the average slop in the initial 50 seconds of the impedance decrease curve, as shown in FIG. 10b. From this figure it can be seen how the larger particle size has a greater rate of impedance decrease for a particular iron particle concentration.

Figure 12:
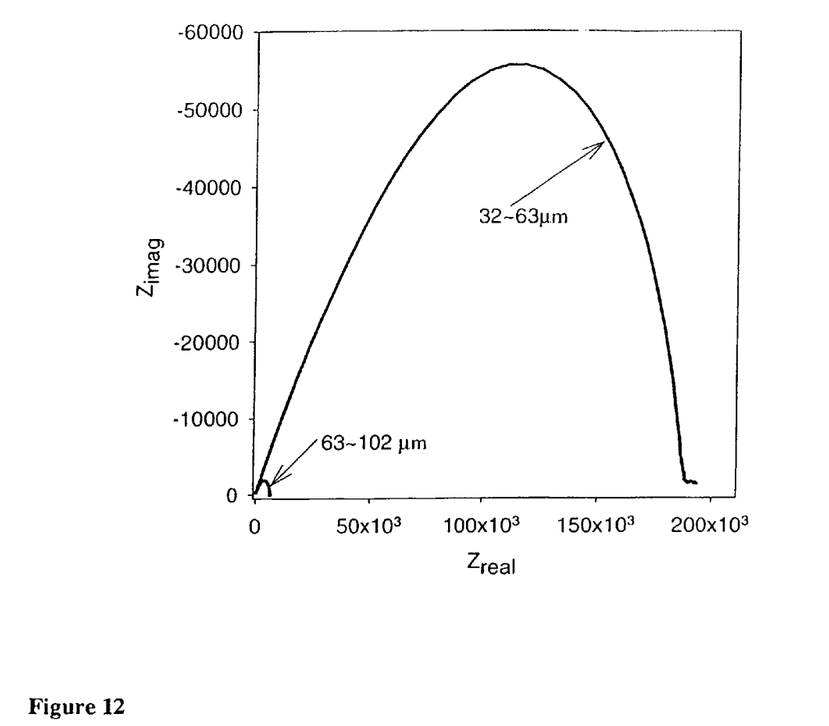
FIG. 12 shows a graphical representation of an impedance spectrum for varying iron particle size in accordance with one embodiment of the invention.

In FIG. 12 the effect of iron particle size on EIS of packed bed in the fully filled gap between the detecting electrodes 12 is shown. It can be seen that for each iron particle size there is a peak imaginary impedance value, which decreases with an increase in particle size.

The position of the imaginary impedance peak also varies in relation to the real impedance value for different iron particle sizes.

From the above it can be seen that by observing the electrical impedance spectrum it is possible to identify size and concentration attributes of iron or ferrous particles in a fluid such as oil.

Before starting the next measurement cycle, the electromagnet should be switched off to release the ferrous particles attracted in the gap between the first set of electrodes. A new measurement is started by switching on the electromagnet and immediately followed by measuring and recording the magnitude of impedance in the gap as a function of time. Recording is stopped when the impedance magnitude reaches a limiting value or changes very slowly with time. Then the electrical impedance spectrum across the fully filled gap is determined by measuring real and imaginary electrical impedance values for a plurality of different frequencies of alternating energy. Characterization parameters, including the peak height, impedance magnitude or real and imaginary component values at selected frequencies are determined from the electrical impedance spectrum and compared with those reference parameters stored for different ferrous particle sizes so as to determine the size of ferrous particles in the gap. The curve of impedance magnitude vs. time is converted into a curve of relative impedance vs. time by dividing the impedance magnitude with that without any ferrous particles in the gap. The rate of impedance decrease is then calculated from the average slop of the curve of relative impedance vs. time in the initial 50 seconds. The rate of impedance decrease is compared with reference rate of impedance decrease stored for different ferrous particle sizes so as to determine the concentration of ferrous particles in the fluid.

Because fluid such as oil includes other contaminants than ferrous particles, the assembly shown in FIG. 1 includes the larger electrodes 11.

By measuring the electrical impedance spectrum across the fluid measurement electrodes 11, information about extraneous matter in the fluid can be identified.

Figure 2:
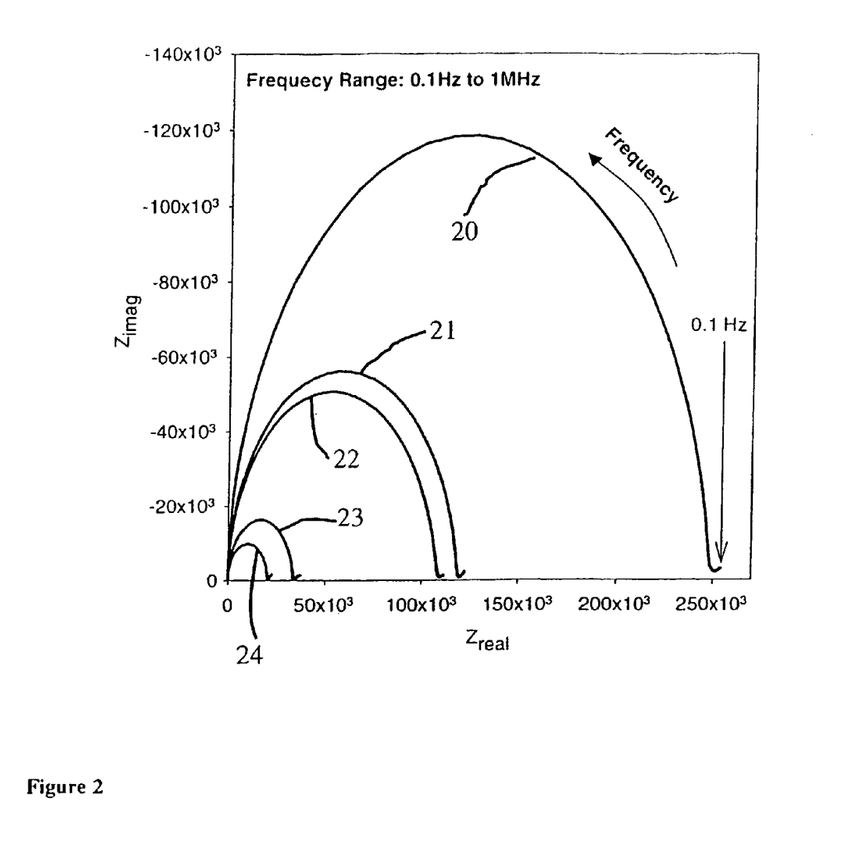
FIG. 2 shows an impedance spectrum showing imaginary impedance versus real impedance for a range of frequencies from 0.1 Hz to 1 MHz in accordance with the first embodiment of the invention.

For example as shown in FIG. 2 the effects of oil type/brand on electrical impedance spectrum of fresh lubrication oils can be ascertained.

For a frequency range of 0.1 Hz to 1 MHz different types of oils represented by references 20, 21, 22, 23, 24 can be obtained. In each case the impedance spectrum produces a peak imaginary impedance value at a particular frequency which drops off on either side of the peak. This graphical or corresponding mathematical representation of the spectra therefore provides a reference curve for particular types of fluids (in this case oils). These reference curves can be established for a range of temperature points.

In order to identify extraneous matter such as gases, oxidates, soot etc. the EIS can be observed to identify extraneous matter such as contaminants in the fluid.

Figure 3:
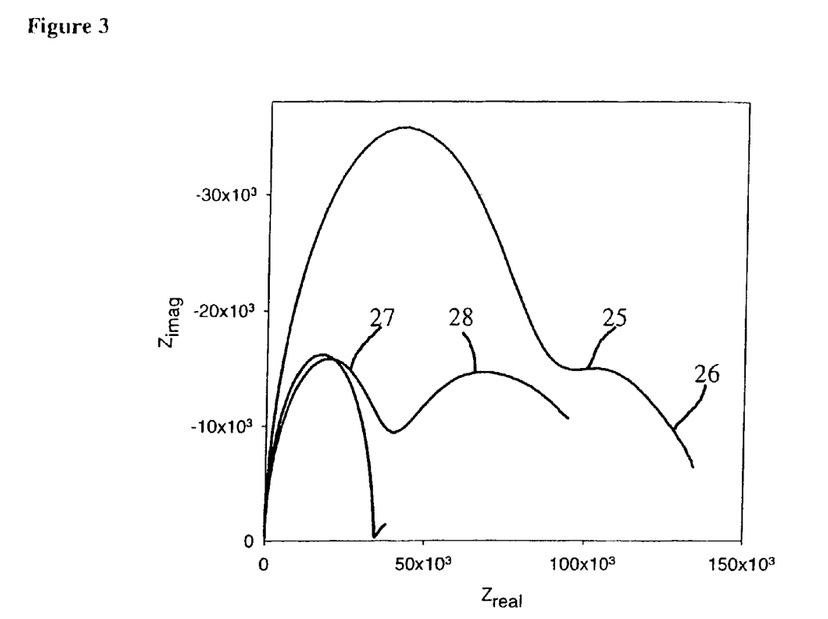
FIG. 3 shows a graphical representation of an impedance spectrum for oil having water contamination according to a second embodiment of the invention.

Therefore as shown in FIG. 3 the EIS for oil having water contamination is shown.

For oil having 0.5% water contamination the impedance spectrum still exhibits a peak but this peak drops off with decreasing frequency value to a stepped region 25 before tailing off through region 26. As the amount of water contamination increases (2% water) the EIS spectrum produces two peaks 27, 28. By observing the number of peaks, their height and their position it is therefore possible to identify whether water is a contaminant.

Figure 4:
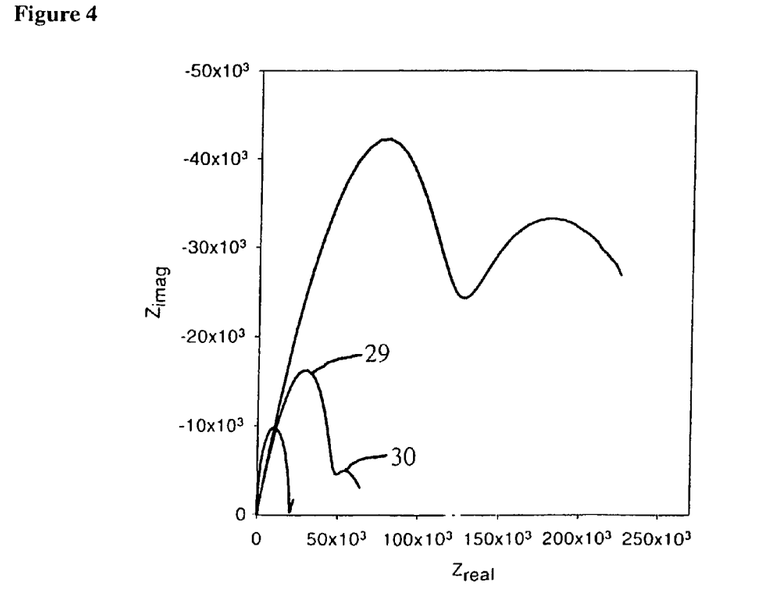
FIG. 4 shows a graphical representation of an impedance spectrum according to a third embodiment of the present invention.

In FIG. 4 an EIS is produced for oil having coolant (ethylene glycol) as a contaminant. In this case for a 0.1% coolant a curve is produced having two peaks of different heights. As the coolant contaminant increases (0.5% coolant) in percentage terms the second peak reduces in size relative to the first peak as referenced by item 29 and 30.

Depending upon the type of oil the shape of the peaks and the difference in height will vary. Thus for some oils contaminated with water or a coolant, the second peak may be greater in height than the first peak. However, by using the uncontaminated EIS curve and comparing this with EIS curves for different amounts of water or coolant contaminant it is possible to identify the amount of water or coolant by comparing a detected EIS curve with prerecorded data showing EIS curves with different water or coolant contamination and matching the detected EIS curve in a field application with the prerecorded EIS curves to obtain a best estimate of the amount of water or coolant contamination.

Figure 5:
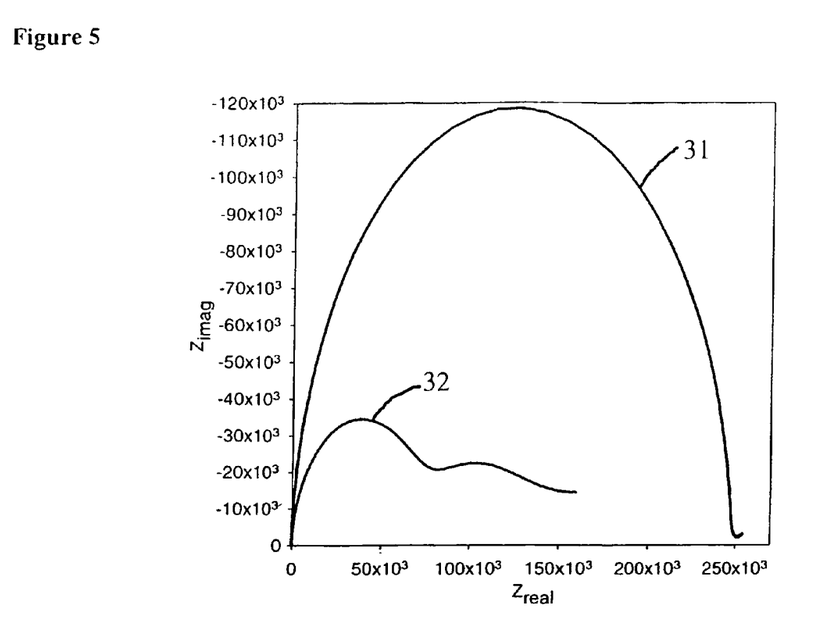
FIG. 5 shows a graphical representation of an impedance spectrum according to a fourth embodiment of the present invention.

FIG. 5 shows another example of EIS curves for an oil having a diesel contaminant. Curve 31 shows the uncontaminated oil curve whereas curve 32 shows the contaminated oil curve.

By obtaining data on how the EIS curves change with diesel contamination it is possible to produce a data base which can be used a reference point for any field testing of oils for diesel contamination.

Figure 6:
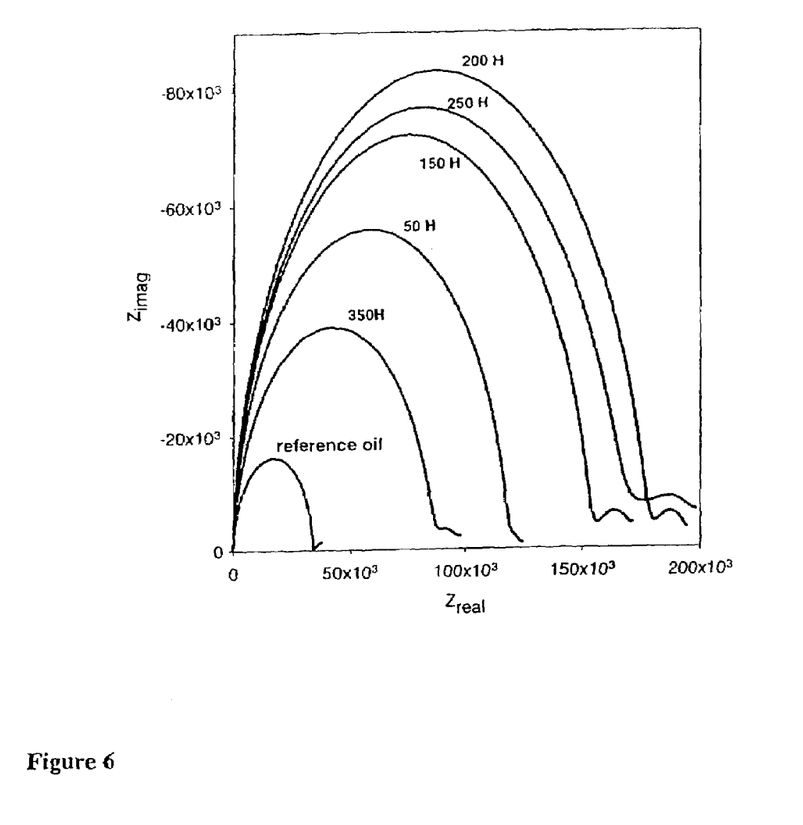
FIG. 6 shows a graphical representation of an impedance spectrum according to a fifth embodiment of the present invention.

FIG. 6 shows the EIS change of oil with usage time in hours. It can be seen that for this particular oil the peak imaginary impedance value increases with usage time till 200 hours then decreases. For other oils the peak values can always decrease with usage time.

Figure 7:
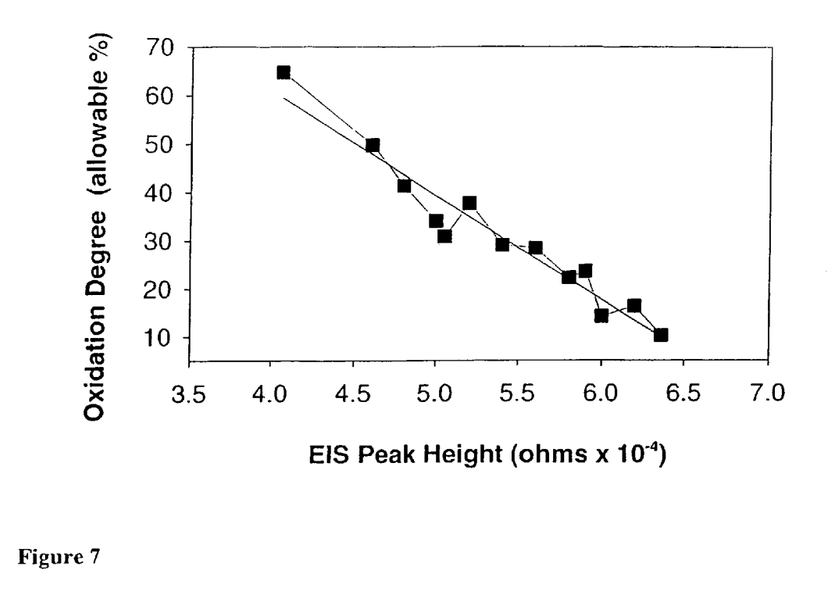
FIG. 7 shows a graphical representation of oxidation degree (allowable %) versus EIS Peak Height (ohms×$10^4$) in accordance with a sixth embodiment of the present invention.

In FIG. 7 a graphical representation is provided of how the EIS peak height in its decreasing stage as shown in FIG. 6 gives an indication of the oxidation degree in allowable percentage. Similar relationship for the peak height increasing stage can be also established. Therefore by observing the peak height of an EIS curve it is possible for a particular oil to identify the degree of oxidation.

Figure 8:
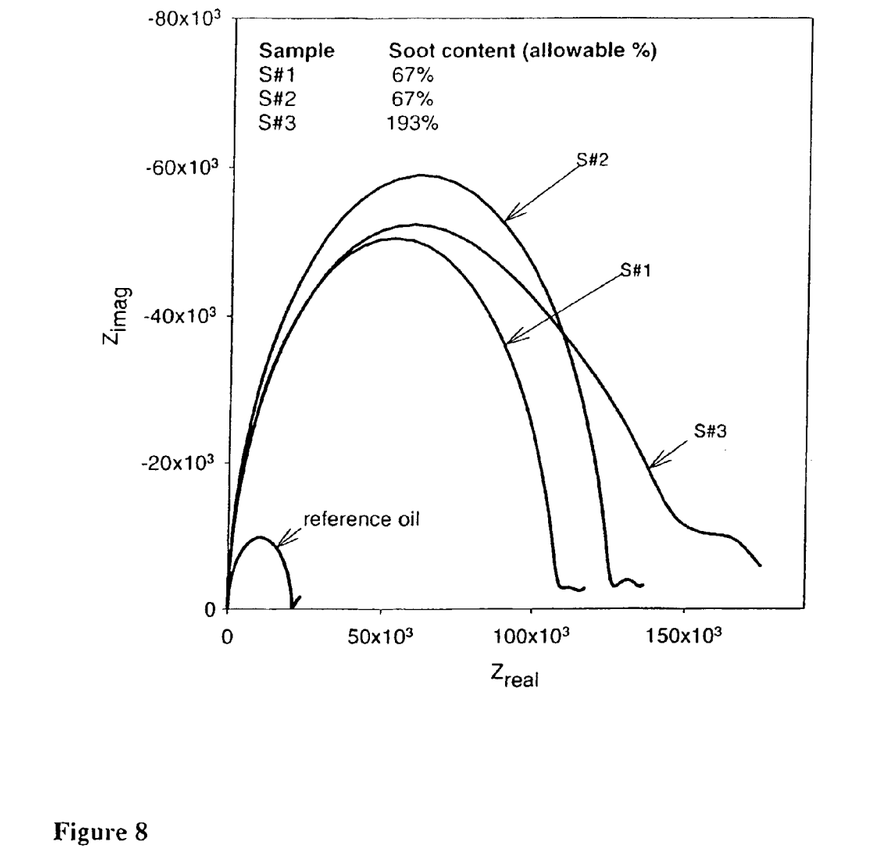
FIG. 8 shows an impedance spectrum according to a seventh embodiment of the present invention.

In FIG. 8 the shape and height of the peak of the EIS curve varies according to soot content. The curves show how the peak is deformed and tails off more with increasing soot content.

Based on observations derived from EIS measurements taken using the aforementioned detection assembly it is possible to employ an automated procedure to identify extraneous matter in oil. This automated procedure which may be implemented by a computer program is described with reference to FIG. 9.

Figure 9:
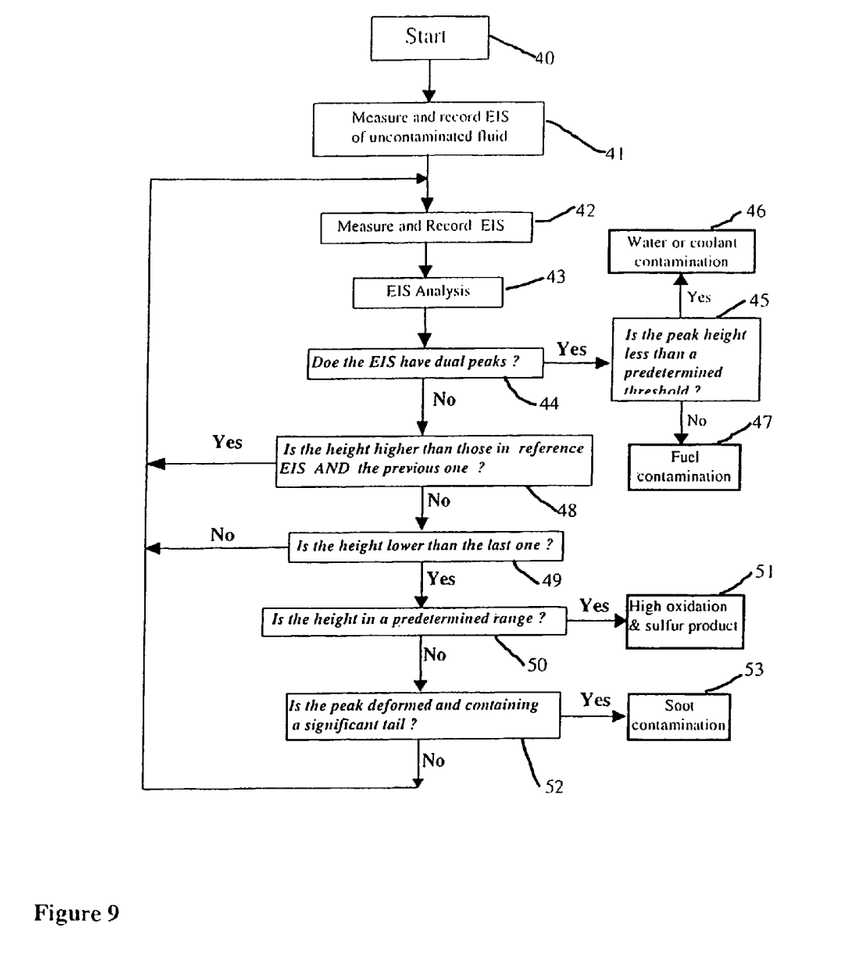
FIG. 9 shows a schematic diagram of a method for detecting and analysing extraneous matter in a fluid according to one embodiment of the present invention.

Once an oil change has occurred referenced by item 40 the electrical impedance spectrum is measured for a range of temperature points and recorded using the aforementioned detection apparatus. If the oil type/brand is right for the particular application as referenced by item 41 a controlling computer is able to activate the detection apparatus so as to measure and record the EIS say every 5 minutes as referenced by item 42. Alternatively if the right type of oil has not been provided an alarm signal is provided to a display to notify an observer that the right type of oil needs to be used.

After the EIS has been measured and recorded the data processor is programmed to calculate the number of peaks and the peak height and characterise the peak shape for each curve produced as referenced by item 43. Then data processor performs data analysis to identify whether the EIS has dual peaks as referenced by item 44. If the answer is yes the data processor is programmed to identify whether the height of the peaks is less than a predetermined threshold, for example 30 k$\Omega$, as identified by item 45. If it is then the data processor is able to produce an output indicating that water or coolant contamination has been identified in the oil, as referenced by item 46. Alternatively if the height is greater than the predetermined threshold an output is produced by the data processor, as referenced by item 47 which indicates that there is diesel fuel contamination. Returning to item 46 if in the alternative the data processor identifies that the EIS does not have dual peaks it performs a comparison step as referenced by item 48, in which the height of the EIS curve measured is compared with those in the base or reference EIS as well as the previous EIS. If the height is greater than both the reference EIS and the EIS from the previous measurement the data processor records this and continues to instruct the detection assembly to measure and record EIS every five minutes. In the alternative if the height is lower than that in the reference EIS or the previous one an additional analysis step is performed in item 49. If the height of the EIS is lower than the previous EIS then an additional analysis is performed by the data processor to identify whether the height of the peak is in a predetermined range, for example 30 to 50 k$\Omega$, as identified by item 50. If the data processor identifies that the height is within this range it produces an output, as referenced by item 51 indicating that high oxidation and sulfur products could be the cause of the contamination.

If the height is not in a predetermined range the data processor analyses the peak to identify whether it is deformed and contains a significant tail, as represented by item 52. If the data processor identifies there is sufficient deformation an output is produced indicating that there is soot contamination, as identified by reference 53.

If there is no peak deformation then the data processor deduces that the oil is not heavily contaminated by any of the previously mentioned contaminants and continues to measure and record EIS in accordance with item 42. Likewise if the height of the peak is lower than the last one as in item 45 the measurement and recording step of item 42 is repeated.

The above procedure can be implemented by using the detector assembly as shown in FIG. 1 with the mini computer 17 appropriately programmed to control the electrical impedance spectrometer to take EIS measurements and to then analyse the EIS results.

It is also possible for the detection assembly to be controlled on-line by remote telemetry for example.

According to another embodiment of the invention the detection assembly can be modified to combine the electrodes into a single bank of electrodes so as to combine detection of iron particles with other extraneous matter.

Although the preferred embodiment of the invention has been described utilising an electronic impedance spectrometer, alternative devices may be used to record real and imaginary impedance values over a range of frequencies. For example a voltage source could be utilised having a variable frequency. An amp meter could then be utilised to measure the change in current. Alternatively an oscilloscope could be utilised to record the impedance spectrum.

What is claimed is:

1. A method for detecting extraneous matter in a fluid including the steps of:
   applying an energy source to electrodes located in a fluid;
   measuring real and imaginary electrical impedance values across the electrodes for a plurality of different frequencies of alternating energy; and
   storing an electrical impedance spectrum curve, which shows changes in real and imaginary impedance measured for a plurality of different frequencies and identifying at least one characteristic of an extraneous matter in fluid from the electrical impedance spectrum curve, including peak height of the electrical impedance spectrum curve.

2. The method as claimed in claim 1 wherein the energy source provides an alternating voltage to the electrodes.

3. The method as claimed in claim 1 wherein electrodes are configured with a plurality of first electrodes connected together and a plurality of second electrodes connected together.

4. The method as claimed in claim 3 wherein the measuring step includes displaying an impedance spectrum in the form of a complex plot of real parts of impedance versus imaginary parts of impedance.

5. The method as claimed in claim 4 including the step of comparing the impedance spectrum measured with a reference impedance spectrum to determine a feature of extraneous matter present in the fluid.

6. The method as claimed in claim 5 including the step of determining at least one type of extraneous matter present in the fluid from a comparison of the measured impedance spectrum relative to a reference impedance spectrum for the fluid without extraneous matter present.

7. The method as claimed in claim 6 wherein the frequency spectrum is measured in the range of 0.1 Hz to 1 MHz.

8. The method as claimed in claim 1, including the step of applying a removable magnetic field across at least one pair of electrodes so as to attract ferrous particles between the electrodes.

9. The method as claimed in claim 8 including the step of storing reference impedance spectra for the fluid for particular extraneous matter.

10. The method as claimed in claim 9 including the step of comparing the measured real and imaginary electrical impedance values with reference real and imaginary electrical impedance values stored for the fluid in memory and outputting the type of extraneous matter present in the fluid if the impedance spectrum measured is substantially the same as one of the impedance spectra stored in memory.

11. The method as claimed in claim 8 including the step of providing a first and a second set of electrodes, the first set for detecting ferrous particles and the second set for detecting other extraneous matter.

12. The method as claimed in claim 11 including the step of providing a magnetic field generation means for generating a magnetic field through a region in which the first set of electrodes is located.

13. The method as claimed in claim 1 including the step of extracting a measured electrical impedance spectrum parameters characterizing the spectrum pattern.

14. A method for detecting extraneous matter in a fluid including the steps of applying an energy source to electrodes located in a fluid, measuring real and imaginary electrical impedance values across the electrodes for a plurality of different frequencies of alternating energy, identifying at least one characteristic of an extraneous matter in the fluid based on changes in the real and imaginary electrical impedance measured for the plurality of different frequencies and determining the number of peaks in an impedance spectrum produced in the measuring step and determining from the or each peak whether a particular extraneous matter is present in the fluid.

15. The method as claimed in claim 14 including the step of determining the height of each impedance spectrum and comparing the height of each peak measured to the height of the or each peak in a reference impedance spectrum for the fluid without extraneous matter so as to determine a type of extraneous matter present in the fluid.

16. The method as claimed in claim 15 including the step of determining whether the height of a peak measured in an impedance spectrum measured during the measuring step is within a predetermined range.

17. The method as claimed in claim 16 including the step of analyzing the impedance spectrum measured to identify whether a peak is present which is deformed and contains a significant tail so as to determine if extraneous matter in the form of soot is present in the fluid.

18. A method for detecting extraneous matter in a fluid including the steps of:
applying an energy source to an electrode located in a fluid, measuring real and imaginary electrical impedance values across the electrodes for a plurality of different frequencies of alternating energy, identifying at least one characteristic of an extraneous matter in the fluid based on changes in the real and imaginary electrical impedance measured from the plurality of different frequencies, producing an impedance spectrum in the form of a complex plot of real parts of impedance versus imaginary parts of impedance and analyzing the impedance spectrum, including peak height, using pattern recognition algorithms to identify the type and/or level of extraneous matter in the fluid.

19. An assembly for detecting extraneous matter in a fluid comprising:
a first set of electrodes located in a fluid chamber, the electrodes being aligned axially with the flow of fluid through the chamber; and
a measuring device connected to the electrodes for measuring real and imaginary impedance values across the electrodes for a plurality of frequencies whereby a data processor is able to store an electrical impedance spectrum curve, showing changes in real and imaginary impedance measured for a plurality of different frequencies and identify at least one characteristic of an extraneous matter from characteristics of the electrical impedance spectrum curve, including peak height, of the electrical impedance spectrum curve.

20. The assembly as claimed in claim 19 including a second set of electrodes located in the fluid chamber and connected to the measuring device for measuring a different extraneous matter to the first set of electrodes.

21. The assembly as claimed in claim 20 wherein the first set of electrodes is located downstream of the second set of electrodes.

22. The assembly as claimed in claim 21 including an adaptor housing with a fluid chamber in which the electrodes are located.

23. A method of analyzing extraneous matter in a fluid including the steps of:
receiving impedance data, the impedance data including real and imaginary impedance values measured across electrodes located in a fluid;
recording the electrical impedance spectrum at a plurality of time intervals;
determining characteristics including peak height of the electrical impedance spectrum from the received impedance data and comparing the characteristics including peak height with a reference impedance spectrum; and
determining a feature of the extraneous matter from the comparing step.

24. The method as claimed in claim 23 including the step of determining how many peaks are present in the electrical impedance spectrum of the received impedance data.

25. The method as claimed in claim 24 including the step of determining whether a particular matter is present by the number of peaks in the electrical impedance spectrum and the height of one or more of the peaks.

26. The method as claimed in claim 24 including the step of determining whether a particular matter is present by determining if the peak of the electrical impedance spectrum is deformed and has a significant tail.

27. The method as claimed in claim 24 including the step of determining whether a particular matter is present by determining whether the height of a single peak is within a predetermined range of real impedance values.

28. The method as claimed in claim 23 including the step of determining whether a particular matter is present in the fluid by determining the change of characterization parameters.

29. A method for detecting a characteristic of ferrous particles in a fluid including the steps of applying a removable magnetic field to fluid in the vicinity of a first set of electrodes to attract ferrous particles into a gap between the electrodes, measuring the magnitude of the impedance across the electrodes as a function of time until the gap is bridged by ferrous particles, measuring real and imaginary electrical impedance values across the electrodes for a plurality of different frequencies of alternating energy and identifying at least one characteristic relating to ferrous particles.

30. The method as claimed in claim 29 wherein the characteristic relating to ferrous particles includes one of the size and concentration of ferrous particles.

31. The method as claimed in claim 30 including the step of removing the magnetic field when the ferrous particles bridge the gap, whereby ferrous particles are released into the fluid before starting the next measuring step.

32. The method as claimed in claim 31 including the step of recording the measured magnitude of impedance across the gap between the first set of electrodes as a function of time and determining whether the gap is fully filled with ferrous particles by observing whether the impedance magnitude reaches a limiting value or changes very slowly with time.

33. The method as claimed in claim 31 including the step of recording a curve of impedance magnitude verses time and converting the curve into a curve of relative impedance.

34. The method as claimed in claim 33 including the step of calculating the rate of impedance decrease from the average slope of the curve of relative impedance verses time in the initial 50 seconds starting from when the magnetic field is applied to the fluid.

35. The method as claimed in claim 34 including the step of determining one or more characterizing parameters of the ferrous particles from the peak height, impedance magnitude or real and imaginary component values at selected frequencies, or from the impedance spectrum measured in the fully filled gap between the first set of electrodes and comparing the or each characterizing parameter with those reference parameters stored for different ferrous particle sizes so as to determine the size of ferrous particles in the gap.

36. The method as claimed in claim 35 including the step of comparing the rate of impedance decrease with reference rate of impedance decrease stored for different ferrous particle sizes so as to determine the concentration of ferrous particles in the fluid.

* * * * *